United States Patent [19]

Chen

[11] 4,177,194

[45] Dec. 4, 1979

[54] TOTAL SYNTHESIS OF THE UTERO-EVACUANT SUBSTANCE D,L-ZOAPATANOL

[75] Inventor: Robert H. K. Chen, Belle Mead, N.J.

[73] Assignee: Ortho Pharmaceutical Corporation, Raritan, N.J.

[21] Appl. No.: 920,432

[22] Filed: Jun. 29, 1978

[51] Int. Cl.$^2$ ............................................. C07D 313/04
[52] U.S. Cl. ............................ 260/333; 260/345.8 R; 260/345.9 R; 260/348.43; 260/348.48; 260/348.62; 568/614; 424/278
[58] Field of Search ........................................ 260/333

[56] References Cited

U.S. PATENT DOCUMENTS

| | | | |
|---|---|---|---|
| 4,086,358 | 4/1978 | Wachter et al. | 260/333 |
| 4,102,895 | 7/1978 | Kanojia et al. | 260/333 |

*Primary Examiner*—Alan L. Rotman
*Assistant Examiner*—Natalia Harkaway
*Attorney, Agent, or Firm*—Benjamin F. Lambert

[57] ABSTRACT

A method of synthesizing 2S*, 3R*-6E-(2-hydroxyethylidene)-2-methyl-2-(4,8-dimethyl-5-oxo-7-nonenyl)-oxepan-3-ol, one of the active ingredients in the zoapatle plant, is described. The natural product is useful as a utero-evacuant agent.

8 Claims, No Drawings

TOTAL SYNTHESIS OF THE UTERO-EVACUANT SUBSTANCE D,L-ZOAPATANOL

The zoapatle plant is a bush about 2 meters high that grows wild in Mexico. Botanically, it is known as *montanoa tomentosa* according to Cervantes, Fam. Compositae, Tribe Heliantheae; another variety of the species is *Montanoa fluoribunda*. The plant is described in great detail in *Las Plantas Medicinales de Mexico*, Third Edition, Ediciones Botas (1944).

The plant has been used for centuries in the form of a "tea" or other crude aqueous preparations primarily as a labor inducer or menses inducer for humans. Its use as a utero-evacuant has been documented in the literature.

In U.S. Pat. No. 4,086,358, a method is described for the isolation of the active ingredients in the zoapatle plant. One of the active ingredients is 2S,3R-6E-(2-hydroxyethylidene)-2-methyl-2-(4,8-dimethyl-5-oxo-7-nonenyl)-oxepan-3-ol. This compound, referred to as zoapatanol, has the following structural formula:

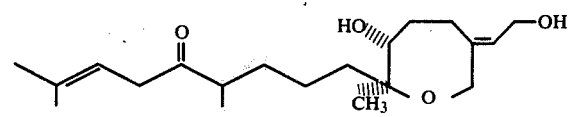

The present invention relates to a method for the total synthesis of 2S*,3R*-6E-(2-hydroxyethylidene)-2-methyl-2-(4,8-dimethyl-5-oxo-7-nonenyl)-oxepan-3-ol. Many of the intermediates employed in the synthesis of zoapatanol are novel compounds and are included as part of the invention.

[*The asterisk indicates the racemic nature of the compound and refers to the relative configuration of the chiral centers.]

The synthesis is comprised of several steps which are summarized in the following schematic diagram:

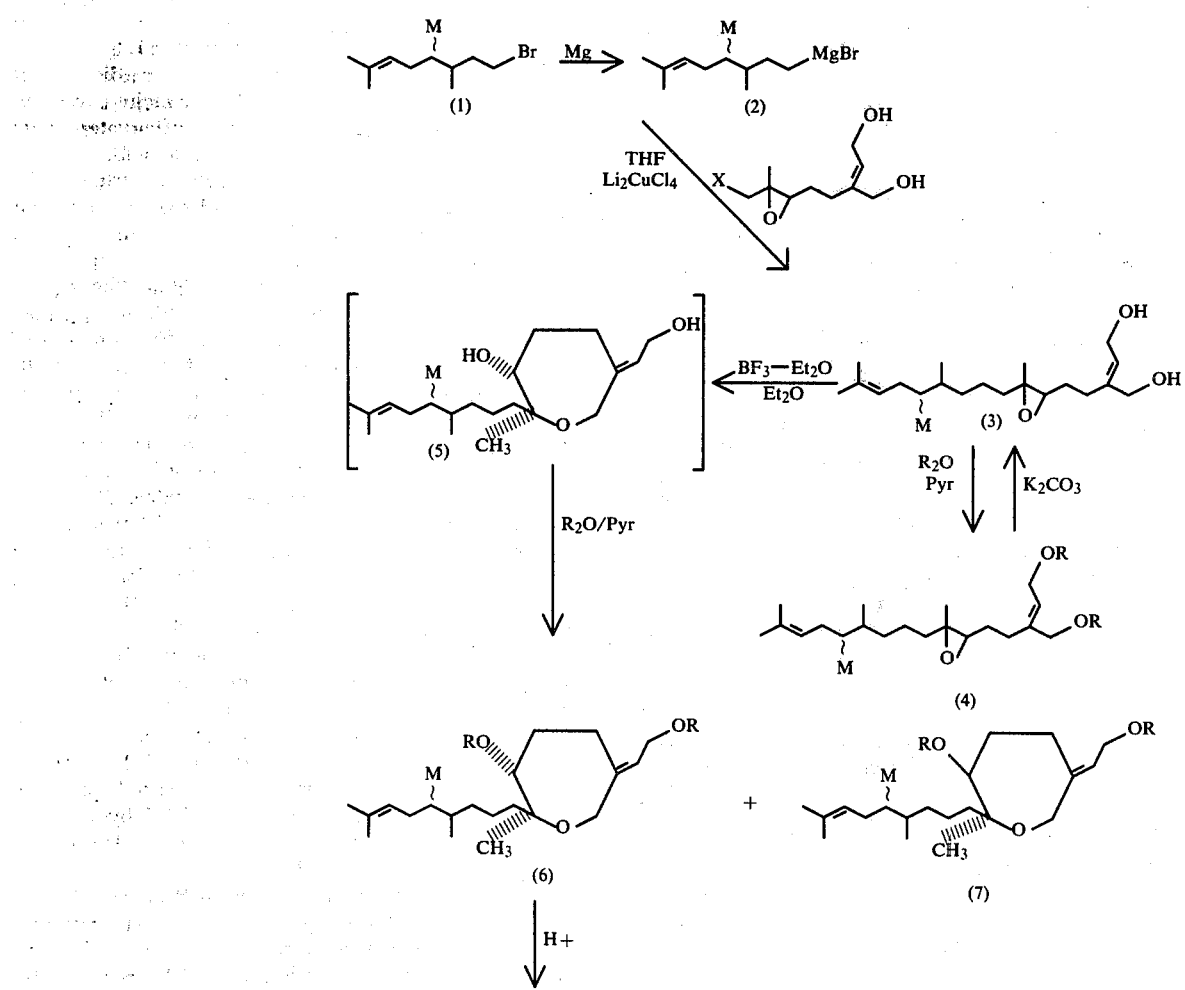

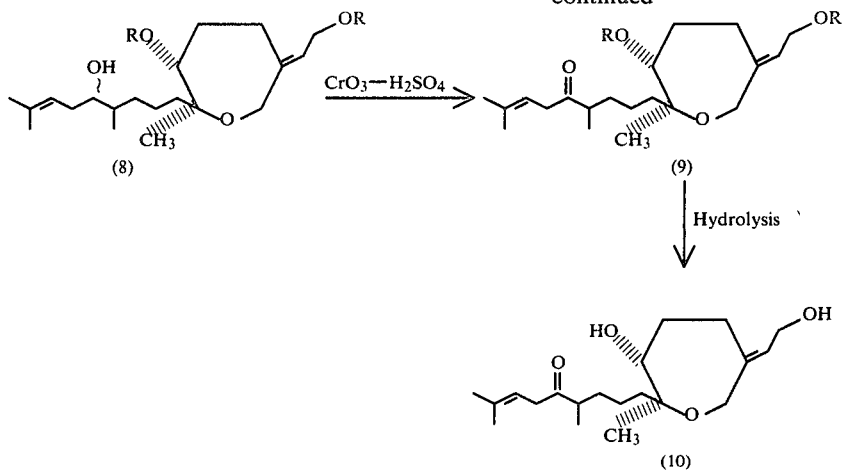

Wherein M is a protecting group selected from the group consisting of an O-tetrahydropyranyl group and an O-ethoxyethyl group, R is an acyl group having 2–5 carbon atoms and X is selected from the group consisting of bromo, chloro, iodo, tosyl, mesyl and brosyl.

As seen from the diagram, the first step in the synthesis involves the preparation of the Grignard reagent (2) from the corresponding halo compound 8-bromo-2,6-dimethyl-5-[2-(tetrahydropyran-2-yloxy)]-2-octene (1). For purposes of describing the invention, the process will be described using a 2-tetrahydropyranyl group as the protecting group. The reaction with magnesium is carried out in the standard fashion, preferably in an organic solvent such as ether or tetrahydrofuran. The Grignard reagent is preferably used in the next step without isolation.

The coupled product (3) is prepared by reacting the Grignard reagent with a substituted 6,7-oxido-2-octen-1-ol. The reaction is carried out in an organic solvent such as ether or tetrahydrofuran at a temperature between about −20° and 0° C. It is preferred to carry out the reaction in the presence of a catalytic amount of a copper salt such as, for example, cuprous iodide, cuprous bromide and lithium copper chloride. The coupled product (3) can be used directly in the cyclization step or it can be purified first by converting it to the diacyl derivative (4) by reaction with a suitable acylating agent such as acetic anhydride in a base such as pyridine.

The product obtained from the coupling reaction (3) is then converted to a mixture of epimeric oxepanes (5) upon treatment with a catalytic amount of a Lewis acid such as boron trifluoride etherate, aluminum chloride, and zinc chloride, for example, or a protic acid such as p-toluenesulfonic acid and trifluoroacetic acid. The reaction may be carried out in an organic solvent such as ether or tetrahydrofuran, for example, at a temperature between about 0° and 30° C. The mixture of oxepanes can also be prepared from the diacyl derivative (4) by first hydrolyzing the ester groups with a mild base such as potassium carbonate, for example, and then reacting the product of the hydrolysis with a Lewis acid.

The mixture of epimeric oxepanes (5) is converted to a mixture of diacyl derivatives (6 and 7) by reaction with an acylating agent such as, for example, acetic anhydride, propionic anhydride or butyric anhydride and acyl halides, such as for example, acetyl chloride, propionyl chloride and butyryl chloride in a basic medium such as pyridine. The mixture of diacyl derivatives is separated by physical means prior to the next step. A preferred method of separation is preparative thin layer chromatography on a suitable adsorbent such as silica gel, alumina or florisil. However, any suitable method of separating the epimeric compounds may be employed. Other suitable methods include column chromatography and high pressure liquid chromatography. The compounds are epimeric at the 3-position.

Hydrolysis of the tetrahydropyranyl derivative (6) to the hydroxyl compound (8) is accomplished by treating the tetrahydropyranyl derivative with an acidic solvent system. Suitable acidic solvent systems include tetrahydrofuran-water-acetic acid, acetonitrile-water-acetic acid, and tetrahydrofuran-water-sulfuric acid.

The acylated derivative (8) is then converted to the derivatized utero-evacuant material (9) by treatment with a suitable oxidizing agent such as, for example, chromium trioxide-sulfuric acid, chromium trioxide-acetic acid or chromium trioxide-pyridine. The oxidation is preferably carried out in a suitable organic solvent such as acetone, 2-butanone, chloroform or methylene chloride. The particular solvent employed will depend upon the particular oxidizing agent employed in the oxidation step. The residue obtained from the oxidation reaction is then converted to the underivatized utero-evacuant material (10) by hydrolysis with a suitable base such as, for example, sodium hydroxide, potassium hydroxide, potassium carbonate and tetra n-butyl ammonium hydroxide. The hydrolysis step is preferably carried out in an organic solvent such as, for example, methanol, ethanol, isopropanol, benzene, ether and tetrahydrofuran. However, aqueous media may also be employed for the hydrolysis step. The reaction is preferably carried out in an inert atmosphere such as, for example, nitrogen or argon. The reaction is generally carried out at room temperature although elevated temperatures such as the reflux temperature of the solvent, for example, may also be employed. The crude product of the hydrolysis can be further purified by column chromatography over an adsorbent material, such as silica gel, alumina or florisil.

The bromo compound, 8-bromo-2,6-dimethyl-5-[2-(tetrahydropyran-2-yloxy)]-2-octene, used to prepare the Grignard reagent in the first step in the synthesis is prepared by a series of reactions using 5-bromo-2-methyl-2-pentene as the starting material. The bromide is first converted to 2-methyl-5-nitro-2-pentene by reaction with sodium nitrite in dimethylsulfoxide. The nitro compound is then reacted with methyl crotonate to form methyl 3,7-dimethyl-4-nitro-6-octenoate. Reaction of the octenoate derivative with titanous chloride results in the formulation of the oxo compound, methyl 3,7-dimethyl-4-oxo-6-octenate. The oxo compound is then reacted with lithium aluminum hydride to form 3,7-dimethyl-4-hydroxy-6-octen-1-ol. The diol is converted to the mono-acetate by reaction with acetic anhydride and the mono-acetate is then converted to the tetrahydropyranyl derivative by reaction with dihydropyran. The tetrahydropyranyl derivative is converted to the corresponding alcohol by reaction with potassium carbonate in a mixture of methanol and water. The bromo compound is then obtained by reacting the alcohol 3,7-dimethyl-4-[2-(tetrahydropyran-2-yloxy)]-6-octen-1-ol with phosphorous tribromide or triphenylphosphine and carbon tetrabromide.

The substituted 6,7-oxido-2-octen-1-ol compound employed to prepare the coupled product (3) is itself prepared by a series of reactions using myrcene as the starting material. 8-Hydroxy-7-methyl-3-methylene-1,6-(E)-octadiene is first synthesized from myrcene by the method of G. Büchi and H. Wüest, *Helv. Chim. Acta*, 50, 2440 (1967). The octadiene compound is then converted to the hydroxy epoxide by reaction with a peracid such as m-chloroperbenzoic acid or peracetic acid. The hydroxy epoxide is then converted to the diacyl derivative by reaction with an equivalent amount of a halogen, such as bromine, followed by an excess of an acetate salt, such as potassium acetate. The major product of the reaction is the compound having the E configuration, however, about 20% of the compound having the Z configuration is also formed. Treatment of the diacyl derivative with a slight excess of p-toluenesulfonyl chloride in the presence of a base affords the corresponding tosylate. Reaction of the tosylate with potassium bromide or sodium bromide in 2-butanone at reflux temperature gives the corresponding bromo derivative. The tosylate or the bromide derivative is then hydrolyzed to the diol, 7-methyl-3-hydroxymethyl-6,7-oxido-8-tosyloxy-(E)-2-octen-1-ol or 7-methyl-3-hydroxymethyl-6,7-oxido-8-bromo-(E)-2-octen-1-ol by treatment with a base such as sodium hydroxide, potassium carbonate or tetra-n-butyl ammonium hydroxide. During the workup of the reaction mixture, the compound having the Z configuration forms a complex with magnesium sulfate which results in a product having only the E configuration. Those compounds wherein X is brosyl and mesyl are prepared in the same manner in which the corresponding tosylate is prepared except that p-bromotoluenesulfonyl chloride and methanesulfonyl chloride are employed in place of p-toluenesulfonyl chloride. The compound (1) wherein M is O-ethoxyethyl is prepared in the same manner as the compound wherein M is O-tetrahydropyranyl except that ethyl vinylether is employed in place of dihydropyran.

The following examples describe the invention in greater detail and are intended to be a way of illustrating and not limiting the invention.

EXAMPLE I

8-Hydroxy-7-methyl-3-methylene-6,7-oxido-1-octene

A solution of sodium acetate (25 g, 0.03 m) in 40% peracetic acid (85 ml) is added to a mixture of 8-hydroxy-7-methyl-3-methylene-1,6-(E)-octadiene (50.0 g, 0.33 m), sodium carbonate (42.4 g, 0.40 m) and methylene chloride (500 ml) at 0°. The resulting mixture is allowed to come to room temperature and is stirred for an additional hour after which it is filtered, diluted with methylene chloride (1 l) and washed with 5% sodium bicarbonate (2 l). The organic layer is dried (Na$_2$SO$_4$), and evaporated in vacuo to give the crude product (49.5 g).

The crude product is purified by column chromatography on silica gel (600 g; ethyl acetate/hexane 1:9) to give 8-hydroxy-7-methyl-3-methylene-6,7-oxido-1-octene (23.2 g, 42%), ir (neat): 3448, 1592 cm$^{-1}$;

nmr (CDCl$_3$) δ:

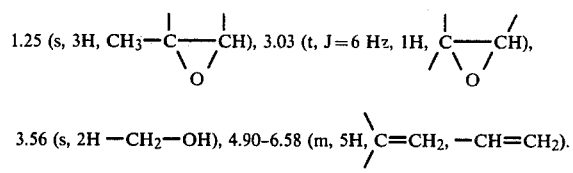

3.56 (s, 2H —CH$_2$—OH), 4.90-6.58 (m, 5H, \C=CH$_2$, —CH=CH$_2$).

EXAMPLE 2

1-Acetoxy-8-hydroxy-7-methyl-3-acetoxymethyl-6,7-oxido-(E)-2-octene

Bromine (56.8 g, 0.355 m) is added to a solution of 8-hydroxy-7-methyl-3-methylene-6,7-oxido-1-octene (59.7 g, 0.355 m) in methylene chloride (1 l) under nitrogen at 0°. The resulting mixture is allowed to warm to room temperature and then washed with water (500 ml). The organic layer is dried (Na$_2$SO$_4$) and the solvent is removed to give the crude dibromide (117.0 g).

A portion of this crude dibromide (57.2 g) in carbon tetrachloride (50 ml) is added to a solution of potassium acetate (59.8 g, 0.61 m) and adogen 464 (15.0 g) in water at 60°. The resulting mixture is stirred overnight, after which it is cooled to room temperature, diluted with ether (1 l) and washed with water (500 ml). The organic layer is dried (Na$_2$SO$_4$) and evaporated in vacuo to give crude diacetate (64.0 g). The crude product is further purified by column chromatography on silica gel (2 kg, ethyl acetate/hexane 4:6) to give 1-acetoxy-8-hydroxy-7-methyl-3-acetoxymethyl-6,7-oxido-(E)-2-octene (9.5 g; 18%).

ir (neat) 3484, 1730 cm$^{-1}$; nmr (CDCl$_3$) δ:

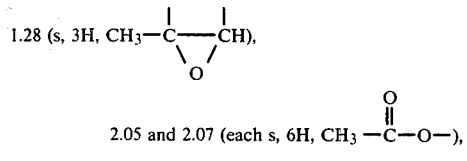

2.05 and 2.07 (each s, 6H, CH$_3$—C(=O)—O—),

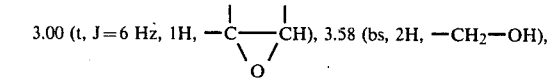

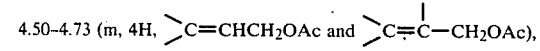

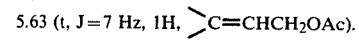

EXAMPLE 3

1-Acetoxy-7-methyl-3-acetoxymethyl-6,7-oxido-8-tosyloxy-(E)-2-octene

Triethylamine (10 ml) and tosyl chloride (13.78 g, 0.072 m) are added to a solution of 1-acetoxy-8-hydroxy-7-methyl-3-acetoxymethyl-6,7-oxido-(E)-2-octene (10.34 g, 0.036 m) in dry tetrahydrofuran (300 ml). The resulting mixture is stirred at room temperature under nitrogen for 6 days. The mixture is then diluted with ether (800 ml) and washed with 5% sodium bicarbonate (800 ml) and water (800 ml). The organic layer is dried ($Na_2SO_4$) and evaporated in vacuo to give the crude product (18.3 g). The crude material is purified by column chromatography on silica gel (600 g; ethyl acetate/hexane; 40:60) to give 1-acetoxy-7-methyl-3-acetoxymethyl-6,7-oxido-8-tosyloxy-(E)-2-octene (10.12 g, 64%).

ir (neat) 1730, 1595 cm$^{-1}$; nmr (CDCl$_3$) δ:

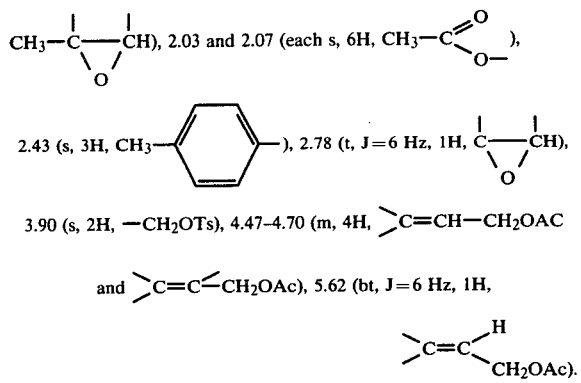

EXAMPLE 4

7-Methyl-3-hydroxymethyl-6,7-oxido-8-tosyloxy-(E)-2-octen-1-ol

A mixture of 1-acetoxy-7-methyl-3-acetoxymethyl-6,7-oxido-8-tosyloxy-(E)-2-octene (4.0 g, 9.1 mmole), methanol (150 ml), water (5 ml) and saturated potassium carbonate solution (5 ml) is stored at room temperature for 2 hours. Most of the methanol is then removed in vacuo and the resulting mixture is extracted with ethyl acetate (3×20 ml). The combined organic layer is dried (MgSO$_4$) and evaporated in vacuo to give an oil (3.4 g). The crude oil is further purified by column chromatography on silica gel (20 g, isopropanol/chloroform 2:98) to give 7-methyl-3-hydroxymethyl-6,7-oxido-8-toxyloxy-(E)-2-octen-1-ol as a colorless oil (2.24 g, 69%).

ir (neat) 3424, 1597 cm$^{-1}$; nmr (CDCl$_3$) δ:

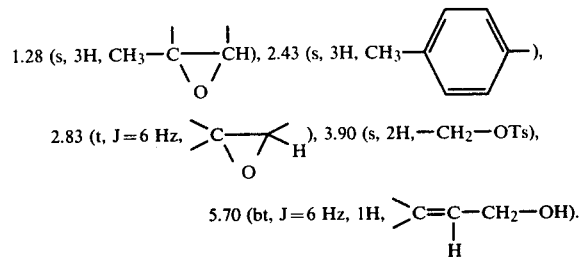

EXAMPLE 5

2-Methyl-5-nitro-2-pentene

5-Bromo-2-methyl-2-pentene (120 g, 0.736 m) is added dropwise to a solution of sodium nitrate (60.9 g, 0.883 m) in dimethylsulfoxide (700 ml) at room temperature under nitrogen. The mixture is stirred for 1 hour and treated with water (500 ml) and petroleum ether (1 l). The organic layer is dried (Na$_2$SO$_4$) and evaporated in vacuo to give a pale yellow liquid (80.7 g). This material is purified by column chromatography on silica gel (800 g, petroleum ether) to give 2-methyl-5-nitro-2-pentene as a colorless liquid (45.4 g, 48%).

ir (neat) 1550 cm$^{-1}$; nmr (CDCl$_3$) δ: 1.70 and 1.73 (both s, 6H, (C$\underline{H}_3$)$_2$—C=C<), 2.50~2.93 (m, 2H, —C$\underline{H}_2$—NO$_2$), 4.35 (t, J=8 Hz, 2H, —CH$_2$—C$\underline{H}_2$—NO$_2$), 5.05 (bt, J=7 Hz, 1H, $\diagdown$C=C$\underline{H}$).

EXAMPLE 6

Methyl 3,7-Diazabicyclo[5,4,0]undec-5-ene (4 ml) is added to a solution of 2-methyl-5-nitro-2-pentene (25.0 g, 0.193 m) in methanol (200 ml). The resulting mixture is heated to 60° and methyl crotonate (30.85 g, 0.308 m) is added under nitrogen. The mixture is then stirred for 6 days at 60° after which it is cooled to room temperature and most of the methanol is removed in vacuo. The residue is treated with ether (500 ml) and washed with 2 N HCl (250 ml) and water (250 ml). The organic layer is dried (Na$_2$SO$_4$) and evaporated in vacuo to give 42.5 g of crude product. The crude product is purified by column chromatography on silica gel (500 g, ethyl acetate/hexane 2:98) to give methyl 3,7-dimethyl-4-nitro-6-octenoate (8.65 g, 42%).

ir (neat): 1736, 1547 cm$^{-1}$; nmr (CDCl$_3$) δ:

1.62 and 1.68 (both s, 6H, (CH$_3$)$_2$C=C$\underline{H}$), 3.67 (s, 3H, —OCH$_3$), 4.22–4.42 (m, 1H, C$\underline{H}$—NO$_2$), 4.95 (bt, J=7 Hz, 1H, $\diagdown$C=C$\underline{H}$).

EXAMPLE 7

Methyl 3,7-dimethyl-4-oxo-6-octenoate

A solution of methyl 3,7-dimethyl-4-nitro-6-octenoate (24.55 g, 0.107 m) in methanol (10 ml) is added dropwise to a solution of sodium methoxide (6.37 g, 0.118 m) in methanol (250 ml) at room temperature under nitrogen. The mixture is stirred for 1 hour, added to a mixture of 20% titanous chloride (170 ml, 0.267 m) and pH 7 buffer (potassium phosphate monobasic sodium hydroxide buffer) solution (340 ml). The resulting mixture is stirred for 30 minutes after which it is treated with ether (1 l). The organic phase is separated, dried (Na$_2$SO$_4$) and evaporated in vacuo to give the crude product (15.4 g). This material is purified by column chromatography on silica gel (300 g, 2% ethyl acetate in hexane) to give methyl 3,7-dimethyl-4-oxo-6-octenoate as a colorless liquid (6.8 g, 35%). ir (neat) 1705 and 1735 cm$^{-1}$; nmr (CDCl$_3$) δ:

1.15 (d, J=7 Hz, 3H, CH₃—CH), 3.2 (bd, J=7 Hz, 2H,

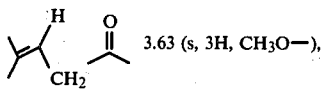   3.63 (s, 3H, CH₃O—), 5.30 (bt, J=7 Hz, 1H, >=CH—).

EXAMPLE 8

3,7-Dimethyl-4-hydroxy-6-octen-1-ol

Methyl 3,7-dimethyl-4-oxo-6-octenoate (68 g, 34 mmole) in ether (10 ml) is added to a mixture of lithium aluminum hydride (1.3 g, 34 mmole) and ether (150 ml) at 0°. After the addition is complete the mixture is allowed to warm to room temperature and stirred for 1 hour, after which it is cooled to 0° and carefully added to a 5% aqueous sodium bicarbonate solution (50 ml). The resulting mixture is treated with water (100 ml) and ethyl acetate (300 ml). The organic phase is separated, dried (Na₂SO₄) and the solvent is removed in vacuo to give a colorless oil (50.6 g, 94%). This material shows one spot on TLC (silica gel 50% ethyl acetate in hexane) and is not further purified.

ir (neat) 3225 cm⁻¹.

EXAMPLE 9

8-Acetoxy-2,6-dimethyl-5-hydroxy-2-octene

A mixture of 3,7-dimethyl-4-hydroxy-6-octen-1-ol (5.06 g, 29 mmole), acetic anhydride (3.06 g, 30 mmole), pyridine (4.75 g, 60 mmole) and ether (100 ml) is stirred at room temperature for 16 hours. The resulting mixture is treated with ether (200 ml) and washed with saturated cupric sulfate solution (2×100 ml). The organic phase is dried (Na₂SO₄) and evaporated in vacuo to give 8-acetoxy-2,6-dimethyl-5-hydroxy-2-octene as a colorless oil (2.27 g, 45%).

ir (neat) 3508; 1738 cm⁻¹; nmr (CDCl₃) δ:

0.93 (d, J=7 Hz, 3H, CH₃—CH), 2.0 (s, 3H, CH₃—C—O—), 4.10 (t, J=7 Hz, 2H, —CH₂—OAc), 5.10 (bt, 1H, >C=CH).

EXAMPLE 10

8-Acetoxy-2,6-dimethyl-5-[2-(tetrahydropyran-2-yloxy)]-2-octene

A mixture of 8-acetoxy-2,6-dimethyl-5-hydroxy-2-octene (2.27 g, 10.6 mmole), dihydropyran (0.98 g, 11.4 mmole), p-toluenesulfonic acid monohydrate (catalytic amount) and ether (50 ml) is stirred at room temperature for 16 hours. The resulting mixture is treated with ether (150 ml) and washed with 5% sodium bicarbonate solution (2×100 ml). The organic phase is dried (Na₂SO₄), and evaporated in vacuo to give the crude product (3.27 g). This material is further purified by column chromatography on silica gel (25 g, 5% ethyl acetate in hexane) to give 8-acetoxy-2,6-dimethyl-5-[2-(tetrahydropyran-2-yloxy)]-2-octene as a colorless oil (2.67 g, 89%).

ir (neat) 1739 cm⁻¹; nmr (CDCl₃) δ:

2.07 (s, 3H, CH₃—C(=O)(O—)), 4.61 (br, 1H, 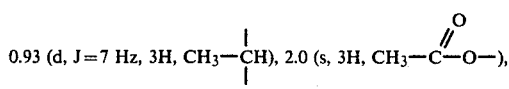), 5.2 (br, 1H, >C=CH).

EXAMPLE 11

3,7-Dimethyl-4-[2-(tetrahydropyran-2-yloxy)]-6-octen-1-ol)

A mixture of 8-acetoxy-2,6-dimethyl-5-[2-(tetrahydropyran-2-yloxy)]-2-octene (2.67 g, 0.5 mmole), saturated potassium carbonate solution (9 ml), water (6 ml) and methanol (100 ml) is stirred for 3 hours at room temperature. Most of the methanol is removed in vacuo and the residue is treated with ethyl acetate (500 ml) and water (200 ml). The organic phase is dried (Na₂SO₄) and evaporated in vacuo to give the crude product (2.5 g). This material is further purified by column chromatography on silica gel (25 g, 15% ethyl acetate in hexane) to give 3,7-dimethyl-4-[2-(tetrahydropyran-2-yloxy)]-6-octen-1-ol as a colorless oil (1.5 g, 60%).

ir (neat) 3434 cm⁻¹, nmr (CDCl₃) δ:

4.62 (br, 1H, [THP]), 5.2 (br, 1H, >C=CH).

EXAMPLE 12

8-Bromo-2,6-dimethyl-5-[2-(tetrahydropyran-2-yloxy)]-2-octene

Triphenylphosphine (1.83 g, 7.02 mmole) in methylene chloride (30 ml) is added to a mixture of 3,7-dimethyl-4-[2-(tetrahydropyran-2-yloxy)]-6-octen-1-ol (1.20 g, 4.7 mmole), carbon tetrabromide (1.94 g, 5.85 mmole), pyridine (2 ml) and methylene chloride (30 ml) at 0° under nitrogen. The mixture is allowed to warm to room temperature and stirred for 4 hours, after which it is treated with methylene chloride (100 ml) and washed with 5% sodium bicarbonate solution. The organic phase is dried (Na₂SO₄) and evaporated in vacuo to give the crude product (5.6 g). This material is further purified by column chromatography on silica gel (100 g, 2% ethyl acetate in hexane) to give 8-bromo-2,6-dimethyl-5-[2-(tetrahydropyran-2-yloxy)]-2-octene as a colorless oil (0..7 g, 46%).

nmr (CDCl₃) δ:

4.61 (br, 1H, [THP]), 5.15 (br, 1H, >C=CH).

EXAMPLE 13

3,7-Dimethyl-4-[2-(tetrahydropyran-2-yloxy)]-6-octenyl magnesium bromide

The Grignard reagent is prepared from 8-bromo-2,6-dimethyl-5-[2-(tetrahydropyran-2-yloxy)]-2-octene (8.5 g, 26.7 mmole) and magnesium (650 mg, 27.1 mmole) in tetrahydrofuran (35 ml) at room temperature under argon. The reagent is not isolated but is used directly in the next step.

EXAMPLE 14

1-Acetoxy-3-acetoxymethyl-7,11,15-trimethyl-12-[2-(tetrahydropyran-2-yloxy)]-(E)-2,14-hexadecadiene An excess of the Grignard reagent is added to a solution of 7-methyl-3-hydroxymethyl-6,7-oxido-8-tosyloxy-(E)-2-octen-1-ol (423.3 mg, 1.3 mmole) in tetrahydrofuran at 0°, followed by Li$_2$CuCl$_4$ (0.1 mmole) and the mixture is stirred for 1.5 hours at 0°. The mixture is allowed to warm to room temperature and then treated with ice water (125 ml) and ethyl acetate (400 ml). The organic phase is separated, dried (Na$_2$SO$_4$) and evaporated in vacuo to give the crude product. This material is then treated with acetic anhydride (10 ml) and pyridine (2 ml) and stirred for 16 hours at room temperature. The resulting mixture is treated with ether (100 ml) and then washed with saturated cupric sulfate solution (100 ml) and 5% sodium bicarbonate solution (100 ml). The organic phase is dried (Na$_2$SO$_4$) and evaporated in vacuo to give an oil (210 mg) which is further purified by column chromatography on silica gel (7 g, 7% ethyl acetate in hexane) to give 1-acetoxy-3-acetoxymethyl-7,11,15-trimethyl-12-[2-(tetrahydropyran-2-yloxy)]-(E)-2,14-hexadecadiene as a colorless oil (41 mg, 9%).

ir (neat) 1735 cm$^{-1}$; nmr (CDCl$_3$) δ:

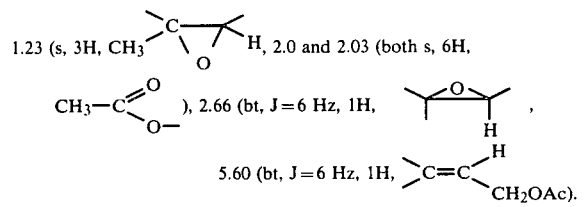

EXAMPLE 15

2S*,3R*-3-Acetoxy-6E-(2-acetoxyethylidene)-2-methyl-2-[4,8-dimethyl-5-(2-tetrahydropyran-2-yloxy)-7-nonenyl]oxepane and 2S*,3S*-3-acetoxy-6E-(2-acetoxyethylidene)-2-methyl-2-[4,8-dimethyl-5-(2-tetrahydropyran-2-yloxy)-7-yloxy-7-nonenyl]-oxepane A mixture of 1-acetoxy-3-acetoxymethyl-7,11,15-trimethyl-12-[2-(tetrahydropyran-2-yloxy)]-(E)-2,14-hexadecadiene (10 mg, 0.02 mmole), methanol (5 ml), saturated potassium carbonate solution (1 ml) and water (1 ml) is stirred at room temperature for 3 hours. The mixture is then treated with ethyl acetate (15 ml) and water (15 ml). The organic phase is dried (Na$_2$SO$_4$) and the solvent is removed in vacuo to give 3-hydroxymethyl-6,7-oxido-12-[2-(tetrahydropyran-2-yloxy)]-7,11,15-trimethyl-(E)-2,14-hexadecadiene-1-ol as a colorless oil. The oil is dissolved in ether (5 ml), treated with boron trifluoride etherate (5 drops) and stirred for 90 minutes at room temperature. The resulting mixture is treated with pyridine (2 ml) and acetic anhydride (1 ml) and stirred for 16 hours. Most of the solvent is evaporated in vacuo and the residue (15 mg) is purified by column chromatography on silica gel (1 g, 20% ether in petroleum ether to give a mixture of 2S*,3R*-3-acetoxy-6E-(2-acetoxyethylidene)-2-methyl-2-[4,8-dimethyl-5-(2-tetrahydro-2-yloxy)-7-nonenyl]-oxepane and 2S*,3S*-acetoxy-6E-(2-acetoxyethylidene)-2-methyl-2-[4,8-dimethyl-5-(2-tetrahydropyran-2-yloxy)-7-nonenyl]-oxepane as a colorless oil (2 mg, 20%). The mixture of compounds is separated by preparative thin layer chromatography (silica gel, 30% ethyl acetate in hexane).

EXAMPLE 16

2S*3R*-3-Acetoxy-6E-(2-acetoxyethylidene)-2-methyl-2-(4,8-dimethyl-5-hydroxy-7-nonenyl)-oxepane 2S*,3R*-3-Acetoxy-6E-(2-acetoxyethylidene)-2-methyl-2-[4,8-dimethyl-5-(2-tetrahydropyran-2-yloxy)-7-nonenyl]-oxepane (2 mg, 0.02 mmole) in tetrahydrofuran (2 ml), water (0.3 ml) and glacial acetic acid (2 drops) is heated at 65° (bath temperature) in a well-capped test tube for 2 hours. The mixture is allowed to cool to room temperature and is treated with ether (10 ml) and water (3 ml). The organic phase is dried (Na$_2$SO$_4$) and the solvent is removed in vacuo to give a colorless oil (1.5 mg). The oil is homogeneous as determined by thin layer chromatography analysis (30% ethyl acetate in hexane).

ir (neat); 3497, 1739 cm$^{-1}$; nmr (CDCl$_3$) δ;

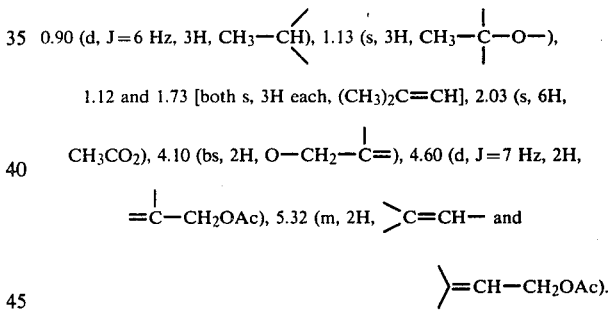

EXAMPLE 17

2S*,3R*-6E-(2-Hydroxyethylidene)-2-methyl-2-(4,8-dimethyl-5-oxo-7-nonenyl)-oxepan-3-ol A. 2S*,3R*-3-Acetoxy-6E-(2-acetoxyethylidene)-2-methyl-2-(4,8-dimethyl-5-hydroxy-7-nonenyl)-oxepane (333 mg) is dissolved in acetone (5 ml) and treated slowly with Jones reagent (2 mmole) at 0° under nitrogen. The resulting mixture is stirred for 7 minutes and then treated with ether (30 ml) and water (20 ml). The layers are separated and the aqueous layer is extracted with ether (20 ml). The combined organic layer is washed with water (30 ml). dried (MgSO$_4$) and evaporated in vacuo to give an oil. The crude product is used as such in the next step.

B. The crude product obtained above (161 mg) is dissolved in tetrahydrofuran (5 ml) and water (5 ml). To this mixture, tetra n-butyl ammonium hydroxide (20% solution in methanol, 1 ml) is added under nitrogen at room temperature and the resulting mixture is stirred for 40 hours. The mixture is treated with ether (50 ml)

and the organic layer is washed with 10% hydrochloric acid (2×15 ml), dried (MgSO₄) and evaporated in vacuo to give an oil. This crude product is purified by chromatography on a SilicAR column (5 g). 2S*,3R*-6E-(2-hydroxyethylidene)-2-methyl-2-(4,8-dimethyl-5-oxo-7-nonenyl)-oxepan-3-ol (81.8 mg) is eluted with ether. Its ir, nmr spectra, R_f on thin layer and retention time on gas chromatography are identical to those of the natural product (Compound I) reported in U.S. Pat. No. 4,086,358. The compound has the following physical analysis:

ir (neat) μ: 2.91 and 5.88.

nmr $_{TMS}{}^{CDCl_3}$ δ:

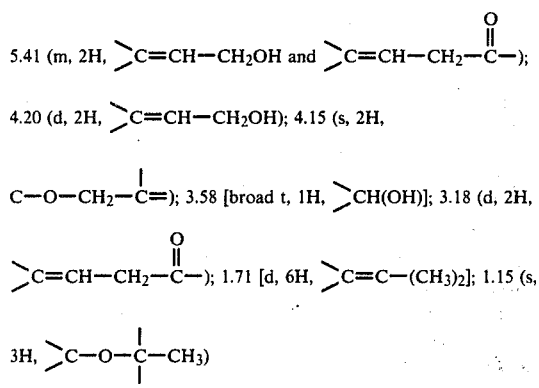

Mass spec [m/e]: 320 [M-18], 251, 233, 221, 171, 143, 141, 137, 125, 113, 97, 95, 81, 69.

Chemical Ionization: M⁺+H=339; M.W.=338.

EXAMPLE 18

8-Acetoxy-2,6-dimethyl-5-[(1-ethoxyethoxy)]-2-octene

A mixture of 8-acetoxy-2,6-dimethyl-5-hydroxy-2-octene (2.27 g, 10.6 mmole), ethyl vinylether (0.82 g. 11.4 mmole), p-toluenesulfonic acid monohydrate (catalytic amount) and ether (50 ml) is stirred at room temperature for 16 hours. The resulting mixture is treated with ether (150 ml) and washed with 5% sodium bicarbonate solution (2×100 ml). The organic phase is dried (Na₂SO₄), and evaporated in vacuo to give the crude product. The crude material is further purified by column chromatography on silica gel (25 g, 5% ethyl acetate in hexane) to give 8-acetoxy-2,6-dimethyl-5-[(1-ethoxyethoxy)]-2-octene as a colorless oil.

EXAMPLE 19

3,7-Dimethyl-4-[(1-ethoxyethoxy)]-6-octen-1-ol

A mixture of 8-acetoxy-2,6-dimethyl-5-[(1-ethoxyethoxy)]-2-octene (0.5 mmole), saturated potassium carbonate solution (9 ml), water (6 ml) and methanol (100 ml) is stirred for 3 hours at room temperature. Most of the methanol is removed in vacuo and the residue is treated with ethyl acetate (500 ml) and water (200 ml). The organic phase is dried (Na₂SO₄) and evaporated in vacuo to give the crude product. This material is further purified by column chromatography on silica gel (25 g, 15% ethyl acetate in hexane) to give 3,7-dimethyl-4-[(1-ethoxyethoxy)]-6-octen-1-ol as a colorless oil.

EXAMPLE 20

8-Bromo-2,6-dimethyl-5-[(1-ethoxyethoxy)]-2-octene

Triphenylphosphine (1.83 g, 7.02 mmole) in methylene chloride (30 ml) is added to a mixture of 3,7-dimethyl-4-[(1-ethoxyethoxy)]-6-octen-1-ol (4.7 mmole) carbon tetrabromide (1.94 g, 5.85 mm), pyridine (2 ml) and methylene chloride at 0° C. under nitrogen. The resulting mixture is allowed to warm to room temperature and stirred for 4 hours after which it is treated with methylene chloride (100 ml) and washed with 5% sodium bicarbonate solution. The organic phase is dried and evaporated in vacuo to give the crude product. This material is further purified by column chromatography on silica gel (100 g, 2% ethyl acetate in hexane) to give 8-bromo-2,6-dimethyl-5-[(1-ethoxyethoxy)]-2-octene as a colorless oil.

EXAMPLE 21

1-Acetoxy-3-acetoxymethyl-7,11,15-trimethyl-12-[(1-ethoxyethoxy)]-(E)-2,14-hexadecadiene The Grignard reagent is prepared from 8-bromo-2,6-dimethyl-5-[(1-ethoxyethoxy)]-2-octene (26 mmole) and magnesium (27.1 mmole) in tetrahydrofuran (35 ml) at room temperature under argon. An excess of the Grignard reagent is added to a solution of 7-methyl-3-hydroxymethyl-6,7-oxido-8-tosyloxy-(E)-2-octen-1-ol (423.3 mg, 1.3 mmole) in tetrahydrofuran at 0° C., followed by Li₂CuCl₄ (0.1 mmole) and the mixture is stirred for 1.5 hours at 0°. The mixture is allowed to warm to room temperature and then treated with ice water (125 ml) and ethyl acetate (400 ml). The organic phase is separated, dried (Na₂SO₄) and evaporated in vacuo to give the crude product. This material is then treated with acetic anhydride (10 ml) and pyridine (2 ml) and stirred for 16 hr. at room temperature. The resulting mixture is treated with ether (100 ml) and then washed with saturated cupric sulfate solution (100 ml) and 5% sodium bicarbonate solution (100 ml). The organic phase is dried (Na₂SO₄) and evaporated in vacuo to give an oil which is further purified by column chromatography on silica gel (7 g, 7% ethyl acetate in hexane) to give 1-acetoxy-3-acetoxymethyl-7,11,15-trimethyl-12-[(1-ethoxyethoxy)](E)-2,14-hexadecadiene as a colorless oil.

What is claimed is:

1. The process for the preparation of a compound of the formula

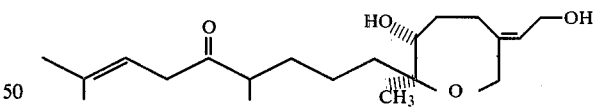

which comprises reacting a compound of the formula

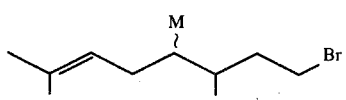

with magnesium to provide a Grignard reagent of the formula

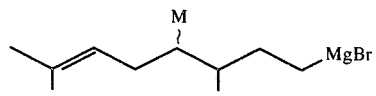

reacting the Grignard reagent with a compound of the formula

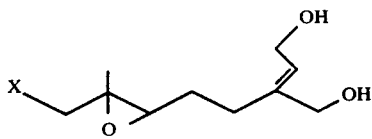

to produce a compound of the formula

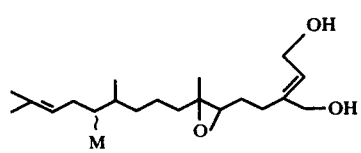

and reacting the product with a Lewis acid or a protic acid to produce a compound of the formula

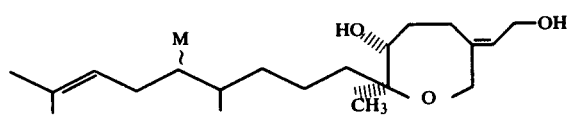

reacting the product with an acylating agent to produce a compound of the formula

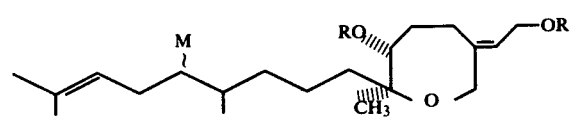

reacting the acylated product with an acid to produce a compound of the formula

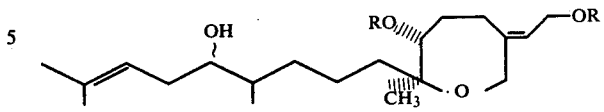

reacting the product with an oxidizing agent to form a compound of the formula

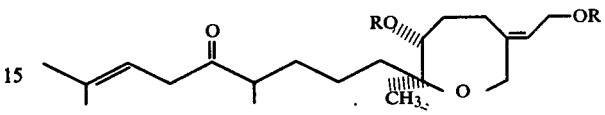

and hydrolyzing the product with a base, wherein R is an acyl group having 2–5 carbon atoms, M is an tetrahydropyran-2-yloxy or 1-ethoxyethoxy group, and X is bromo, chloro, iodo, tosyl, mesyl and brosyl.

2. The process of claim 1 wherein the Lewis acid is boron trifluoride etherate.

3. The process of claim 1 wherein the protic acid is p-toluenesulfonic acid.

4. The process of claim 1 wherein the acylating agent is acetic anhydride.

5. The process of claim 1 wherein the oxidizing agent is chromium trioxide-sulfuric acid.

6. The process of claim 1 wherein the base is tetra n-butyl ammonium hydroxide.

7. The process of claim 1 wherein M is tetrahydropyran-2-yloxy.

8. The process of claim 1 wherein X is tosyl.

* * * * *